United States Patent [19]
Hoff

[11] 3,993,058
[45] Nov. 23, 1976

[54] INTRAUTERINE DEVICE WITH SEEKER FOR FINDING THE CERVICAL OS AND HOUSING MEMBER FOR FITTING DEVICE IN AN INSERTER

[75] Inventor: Seymour Hoff, San Jose, Calif.

[73] Assignee: Alza Corporation, Palo Alto, Calif.

[22] Filed: June 23, 1975

[21] Appl. No.: 589,270

Related U.S. Application Data

[63] Continuation-in-part of Ser. No. 499,186, Aug. 21, 1974, abandoned.

[52] U.S. Cl. .............................. 128/130; 128/260
[51] Int. Cl.² .......................................... A61F 5/46
[58] Field of Search ........................ 128/127–131, 128/260, 267

[56] References Cited
UNITED STATES PATENTS

| | | |
|---|---|---|
| 3,253,590 | 5/1966 | Birnberg et al. ............ 128/130 |
| 3,515,132 | 6/1970 | McKnight ................... 128/130 |
| 3,533,406 | 10/1970 | Tatum ..................... 128/267 X |
| 3,820,535 | 6/1974 | Marco ....................... 128/130 |
| 3,840,005 | 10/1974 | Walker ...................... 128/130 |

Primary Examiner—Lawrence W. Trapp
Attorney, Agent, or Firm—Paul L. Sabatine; Edward L. Mandell; Thomas E. Ciotti

[57] ABSTRACT

Intrauterine device with a seeker and housing member is disclosed. The seeker is a curved-wall member positioned at the lead end of the device for finding, and guiding the device into the external cervical os. The housing member is positioned at the trailing end of the device and it has a smaller diameter than the device for receiving a thread and for presenting a smaller mass to an inserter.

6 Claims, 4 Drawing Figures

3,993,058

INTRAUTERINE DEVICE WITH SEEKER FOR FINDING THE CERVICAL OS AND HOUSING MEMBER FOR FITTING DEVICE IN AN INSERTER

CROSS REFERENCE TO RELATED APPLICATION

This application is a continuation-in-part of my abandoned copending United States Patent Application Ser. No. 499,186, filed on Aug. 21, 1974, which application is assigned to the same assignee of this application, and benefit of its filing date is hereby claimed.

FIELD OF THE INVENTION

This invention relates to an intrauterine device. More particularly the invention concerns an intrauterine device having an improvement at its lead end for finding and entering the external cervical os, and an improvement at its trailing end for attaching a thread and for presenting a smaller volume to an inserter.

BACKGROUND OF THE INVENTION

The intrauterine device is close to an ideal contraceptive device. Although it requires clinical insertion, the device is not related to coitus, requires only occasional replacement, and it provides inexpensive long term protection against pregnancy.

Medical research focused therefore on improving the performance of the device by reducing the incidences of involuntary expulsion and unwanted pregnancy, in eliminating uterine discomfort and in studies pertaining to the optimal size and configuration of the device itself. One such device made available by medical research and in commercial use, comprises a transverse member and a longitudinal member dependent therefrom substantially defining a T-shaped device.

While progress has been made in improving this device in a few selected parameters, there is no reported effort directed to improving the device for, one, making it easier for finding the external cervical os with subsequent passage through the canal for eventual high fundal placement, and two, housing the device in an inserter. Additionally, the prior art unimproved T-shaped device presents a large structural posture which increases the probability of harming the fragile cellular wall of the cervical os and enhances the likelihood of pain and trauma that can accompany the insertion of the device. Thus, in view of the foregoing, it will be readily appreciated by those versed in the subject science, that if an improved device is made available for making it easier for finding and entering the external cervical os, and for housing the device in an inserter, such improvements would increase the usefulness of the device, and also represent a valuable contribution to contraceptive science.

SUMMARY OF THE INVENTION

Accordingly, it is an immediate object of the present invention to provide an improved intrauterine device that overcomes the difficulties associated with the prior art.

Yet another object of the invention is to provide an improvement in an intrauterine device that is inexpensive to manufacture and easy to use for properly positioning a device in the uterine cavity.

Another object of the invention is to provide an intrauterine device having an improvement at its lead end that on contact with the external cervical os stabilizes the device and guides it into the uterus.

Yet another principal object of the invention is to make available to the art an intrauterine device having a leading end with an external cervical os seeker attached thereto. The device with its seeker, when placed in the vagina abutting the external cervical os, facilitates the insertion procedure while simultaneously decreasing the incident of pain and discomfort frequently associated with the prior art devices.

Still yet another principal object of the invention is to provide an intrauterine device having at its trailing end a housing member having a smaller diameter than the rest of the device for fixing a thread thereto while simultaneously reducing the volume of the trailing end of the device for presenting a reduced mass to the inside of an inserter when the device is housed in an intrauterine inserter.

Yet another primary object of the invention is to provide an intrauterine device comprised of a seeker at its lead end and a housing member at its trailing end which act in concert for improved uterine insertion and for substantially reducing the occurrence of cervical and uterine wall penetrations.

The above and other objects of the present invention will become more apparent from a reading of the following description, taken in conjunction with the drawings which illustrate the invention and the accompanying claims.

BRIEF DESCRIPTION OF THE DRAWINGS

In the drawings, which are not drawn to scale, but are set forth to illustrate various embodiments of the invention, the figures are as follows.

In the drawings and specification, like parts in related figures are identified by like numbers. The terms appearing earlier in the specification and in the description of the drawings, as well as embodiments thereof, are further described elsewhere in the disclosure.

DETAILED DESCRIPTION OF THE DRAWINGS

Figure 1:
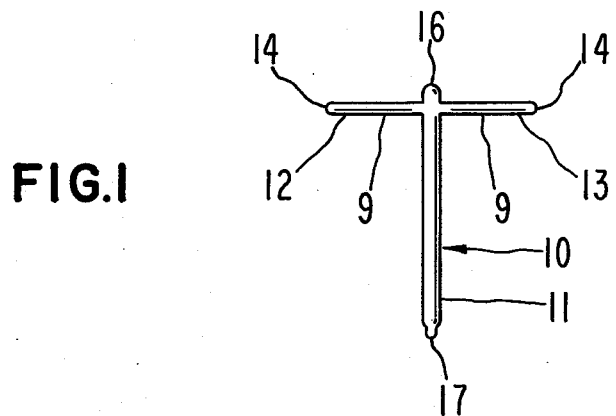
FIG. 1 is a partly diagrammatical frontal elevational view of an improved intrauterine device of the invention.

Turning now to the drawings in detail, which are examples of an improved intrauterine device according to the invention, and which examples are not to be construed as limiting, one embodiment of a novel device is indicated in FIG. 1 by the number 10. In FIG. 1, device 10 is comprised of a transverse member 9 suitably fixed to a longitudinal, dependent member 11. Member 11 may be linear or curved and it has a lead end 15 and a distant end 17. Member 9 interconnects with dependent member 11 at lead end 15 with member 9 extended outwards in two directions from member 11 to define a pair of arms, including arm 12 and arm 13, a right and left arm respectively. Arms 12 and 13 are linear or curved-linear and each terminates in a rounded end 14 to prevent any possible damage to the endometrial wall of uterine cavity 1, as seen in FIG. 3.

Figure 2:
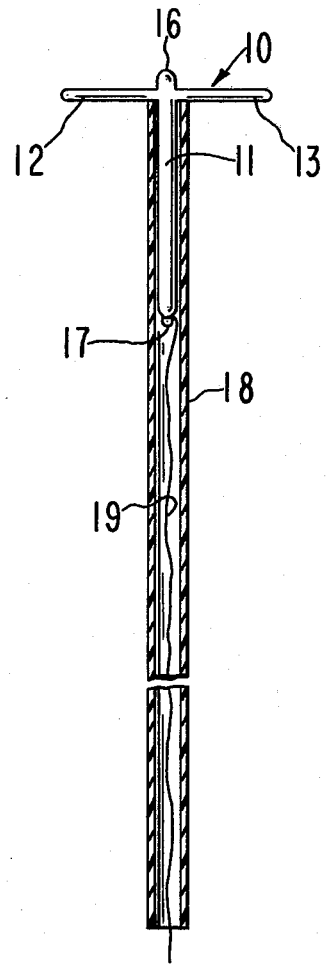
FIG. 2 is a sketch illustrating the device housed in an inserter.

Lead end 15 extends above transverse member 9 to form an external cervical os seeker 16. Seeker 16 axis is co-extensive with the axis of longitudinal member 11 and it assists the physician in finding the external cervical os 3 as seen in FIG. 2. This also aids in better uterine placement. Seeker 16 has a non-traumatizing curved or rounded-shaped configuration and it can be integrally formed or suitably fixed to lead end 15. In one embodiment seeker 16 is formed of a wall material continuous with the wall of transverse member 9. In another embodiment, seeker 16 is a curved-wall extension of rounded longitudinal member 11 and it has an internal diameter that substantially corresponds to the internal diameter of the longitudinal member 11. The curved wall of seeker 16 can have a configuration selected from the group consisting of dome, oval, ellipse, circle, and like non-traumatizing shapes. Longitudinal member 11 has a substantially uniform diameter from its lead end 16 extended to its distant trailing end where it terminates in improved housing member 17. Member 17 is formed continuous with the trailing end of longitudinal member 11 and it has a smaller diameter than longitudinal member 11. The reduced diameter, as seen in FIG. 2, is for attaching thread 19 and for simultaneously presenting a smaller mass to inserter 18 when device 10 is housed in inserter 18. Thread 19 is for removing device 10 from a uterus. Housing member 17 has a domed, oval, rounded, elliptical, half-circle, and like non-traumatizing shape. The improvement of member 17 prevents device 10 from jamming or from fitting too tightly in an inserter, thereby substantially avoiding jamming and improper placement of the device and damage to the uterine cavity. Device 10 is substantially T-shaped or arrow-shaped and it is sized and shaped to fit all uterine cavities. Its dimensions can be made to conform to nulliparous and multiparous adult female uterine cavities. Generally, member 9, whether perpendicular to or skewed from member 11, has a length of 20 to 40 millimeters, measured from the ends of the arms, and a diameter of 1 to 4 millimeters. Generally, member 11 also has a length from end to end of 20 to 40 millimeters and a diameter of 1 to 4 millimeters, except at its trailing end where it is smaller than the diameter immediately above and adjacent thereto. For household pets, farm and sport animals, device 10 can be dimensioned to the appropriate size. An intrauterine device similar to the above-described device, but totally devoid of the improvement comprising inventive seeker 16 and the smaller end 17, is disclosed in U.S. Pat. No. 3,533,406.

Figure 3:
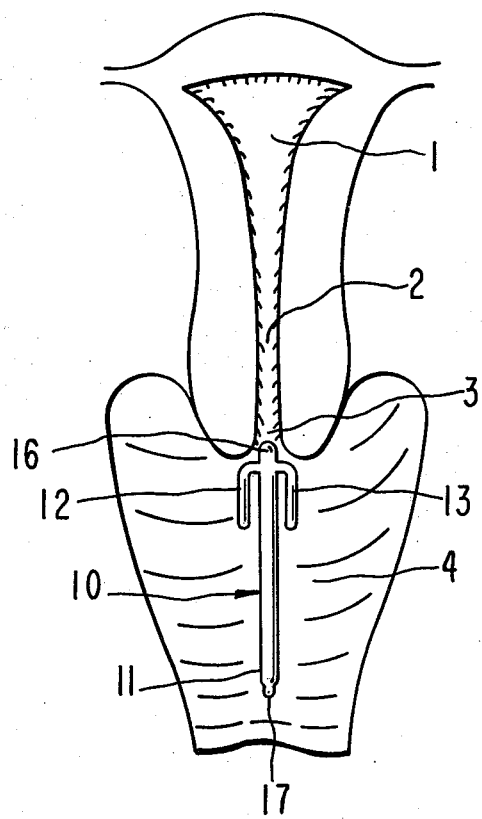
FIG. 3 is a sectional view of the uterine cavity showing an improved intrauterine device in proper position for entering the external cervical os.

In FIG. 3, there is depicted device 10 with arms 12 and 13 folded down and against dependent member 11 for admission into uterine cavity 1 through cervical canal 2. In FIG. 3, device 10 is seen in vagina 4 with seeker 16 finding and abutting cervical os 3. In operation, seeker 16 stabilizes and guides device 10 into os 3 for improved, effective and comfortable insertion and placement substantially free of uterine perforations.

Intrauterine device 10 of the invention can also be a source of antifertility agent. In one embodiment, the agent is a wire made of a member selected from the group consisting of copper and zinc and mixtures thereof, twisted around device 10. These metals and alloys also can be applied on device 10 by coating, encasing transverse 9 and/or dependent member 11 in a metal sleeve, or the like. The use of copper and zinc as a contraceptive agent is disclosed in U.S. Pat. No. 3,563,235. The amount of agent on the exposed surface of a device is about 25 to 400 mm$^2$, for releasing a contraceptively effective amount of copper ion, zinc ion or a mixture thereof when placed in a fertile uterine cavity.

Figure 4:
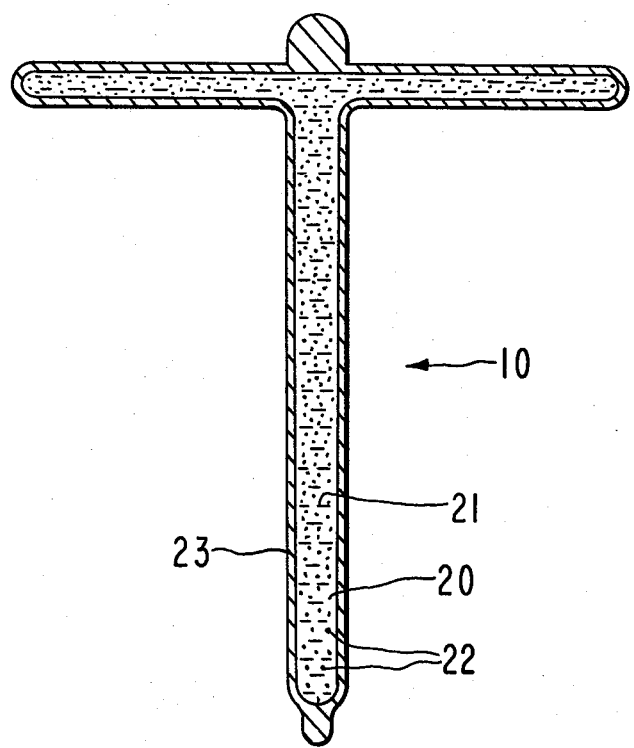
FIG. 4 is a sectional view of the intrauterine device showing a housing therein.

Improved uterine device 10 also can be fabricated with a reservoir housed in the device as seen in FIG. 4. The reservoir 20 contains a carrier and an antifertility agent. The material suitable for use as the carrier 21 is permeable to the passage of the agent 22 and it contains an agent or a mixture of agents. The wall 23 of this kind of device is formed of a material permeable to the passage of the antifertility agent but at a lower rate than through the carrier. In operation, agent dissolved in the carrier is released from the device by diffusion through the wall at a rate controlled by the wall.

Carriers suitable for the present purposes include propylene glycol, silicone oil, glycerin, corn oil, and the like. Materials suitable for the wall of a reservoir device include vinylchloride diethyl fumurate, poly(dimethylsiloxane), cross-linked partially hydrolyzed insoluble poly(vinyl alcohol), and the like.

Antifertility agents suitable for use with these devices include progestational agents and estrogenic agents, such as pregn-4-ene-3,20-dione; 19-nor-pregn-4-ene-3,20-dione; dl-11$\beta$-ethyl-17-ethynyl-17$\beta$-hydroxygen-4-ene-3-one; 17$\beta$-estradiol; ethynyl estradiol; and the like. The amount of the above agent present in a reservoir is usually 20 mg to 300 mg for release at a rate of 20 $\mu$g to 300 $\mu$g per day for 3 months to 3 years, to a fertile uterus of a potential child-bearing, 90 to 180 lb. adult woman.

It will be understood by those versed in the art in the light of the present specification, drawings and accompanying claims, that this invention makes available to the art both a novel and useful intrauterine device graced with a means for intimately seeking and contacting the external cervical os and for enhancing the housing of the device in an inserter for better release therefrom. And, while the improved seeker and the reduced housing mass can be used with devices that release an antifertility agent and with non-releasing devices, it will be further understood by those versed in the art that many different embodiments of this invention can be made without departing from the scope of the invention. Accordingly, it is to be understood the invention is not to be construed as limited, but it embraces all equivalents inherent therein.

I claim:

1. An improved intrauterine device adapted for easy insertion and prolonged placement in a fertile uterus, the device consisting of a transverse member, a longitudinal member dependent upon the transverse member and suitably united thereto with the longitudinal member having a substantially uniform internal diameter, a lead end formed where the transverse and longitudinal members unite, a trailing end distant from the lead end on the longitudinal member, the improvements consisting essentially of a seeker member having a curved surface raised above the plane of the transverse member continuous with the lead end and having an external diameter substantially equal to the external diameter of the longitudinal member, and a housing member formed continuous with the trailing end of the longitudinal member and having an external diameter smaller than the diameter of the longitudinal member.

2. The improved device according to claim 1 wherein the seeker has its axis coextensive with the axis of the longitudinal member, and wherein the seeker enhances finding the external cervical os and concomitantly stabilizes and guides the device thereto.

3. The improved device according to claim 1 wherein the housing member has its axis coextensive with the axis of the longitudinal member and wherein the housing member presents a reduced mass to an inserter when the device is housed therein.

4. The improved device according to claim 1 wherein the transverse member is substantially linear and the seeker is formed continuous with said member.

5. The improved device according to claim 1 wherein the longitudinal member is substantially linear and the seeker is formed continuous with said member.

6. The improved device according to claim 1 wherein the device is sized to fit nulliparous and multiparous uterine cavities.

* * * * *